United States Patent
Yabuhara et al.

(10) Patent No.: US 9,494,496 B2
(45) Date of Patent: Nov. 15, 2016

(54) SOLID-PHASE EXTRACTION APPARATUS AND VISCOSITY MEASUREMENT APPARATUS

(75) Inventors: Tadao Yabuhara, Tokyo (JP); Shinya Ito, Tokyo (JP); Izumi Waki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 431 days.

(21) Appl. No.: 14/131,248

(22) PCT Filed: Apr. 16, 2012

(86) PCT No.: PCT/JP2012/060204
§ 371 (c)(1),
(2), (4) Date: Jan. 23, 2014

(87) PCT Pub. No.: WO2013/008502
PCT Pub. Date: Jan. 17, 2013

(65) Prior Publication Data
US 2014/0137671 A1  May 22, 2014

(30) Foreign Application Priority Data
Jul. 8, 2011  (JP) ................................. 2011-151982

(51) Int. Cl.
*G01N 1/40* (2006.01)
*G01N 1/34* (2006.01)
(Continued)

(52) U.S. Cl.
CPC ................ *G01N 1/34* (2013.01); *B01L 3/021* (2013.01); *G01N 1/405* (2013.01); *G01N 11/00* (2013.01);
(Continued)

(58) Field of Classification Search
None
See application file for complete search history.

(56) References Cited

U.S. PATENT DOCUMENTS 5,257,529 A * 11/1993 Taniguchi .............. G01N 11/04
                                                73/54.04
5,272,912 A * 12/1993 Katsuzaki .............. G01N 11/04
                                                73/54.08

(Continued)

FOREIGN PATENT DOCUMENTS

EP      0 608 425 A1    8/1994
GB      2 184 368 A     6/1987

(Continued)

OTHER PUBLICATIONS

Japanese Office Action received in corresponding Japanese Application No. 2013-523846 dated Jan. 6, 2015.

(Continued)

*Primary Examiner* — Robert R Raevis
(74) *Attorney, Agent, or Firm* — Mattingly & Malur, PC (57) ABSTRACT

A solid-phase extraction apparatus capable of carrying out highly accurate solid-phase extraction by automatically controlling liquid-permeation speeds in an adsorbing step, a cleaning step, and an eluting step of the solid-phase extraction in order to improve the accuracy of the collection rate of a measurement component(s) also in measurement of each of sample solutions respectively having different viscosities and to ensure a certain processing ability. The solid-phase extraction apparatus includes a sample dispensing unit that dispenses a sample solution, a solid-phase extraction unit that carries out a solid-phase extraction process of applying a pressure to the sample solution dispensed by the sample dispensing unit and extracting the measurement component from the sample solution, and a converting unit that measures the viscosity of the sample (Continued)

solution and determines the pressure to be applied to a solid-phase extraction cartridge based on the information of the measured viscosity of the sample solution.

10 Claims, 7 Drawing Sheets

(51) Int. Cl.
　　*G01N 11/00*　　(2006.01)
　　*G01N 35/02*　　(2006.01)
　　*B01L 3/02*　　(2006.01)

(52) U.S. Cl.
　　CPC ......... *G01N 35/02* (2013.01); *B01L 2200/146* (2013.01); *B01L 2200/148* (2013.01)

(56) References Cited

U.S. PATENT DOCUMENTS

| | | | |
|---|---|---|---|
| 5,324,480 A * | 6/1994 | Shumate et al. | 422/63 |
| 5,452,619 A | 9/1995 | Kawanabe et al. | |
| 5,488,874 A | 2/1996 | Kawanabe et al. | |
| 5,660,792 A | 8/1997 | Koike | |
| 2005/0045533 A1 * | 3/2005 | Fujimoto et al. | 210/90 |
| 2007/0110586 A1 | 5/2007 | Yamakawa | |
| 2010/0139375 A1 * | 6/2010 | Johns et al. | 73/54.24 |
| 2011/0065101 A1 * | 3/2011 | Bell et al. | 435/6 |
| 2012/0058009 A1 | 3/2012 | Nogami et al. | |

FOREIGN PATENT DOCUMENTS

| | | |
|---|---|---|
| JP | 56-164957 A | 12/1981 |
| JP | 05-107174 A | 4/1993 |
| JP | 08-164302 A | 6/1996 |
| JP | 10-090281 A | 10/1998 |
| JP | 2005-110670 A | 4/2005 |
| JP | 2006-007081 A | 1/2006 |
| JP | 2006-153850 A | 6/2006 |
| JP | 2008-215859 A | 9/2008 |
| WO | 2006/025557 A1 | 3/2006 |
| WO | 2010/100816 A1 | 9/2010 |

OTHER PUBLICATIONS

European Search Report received in corresponding European Application No. 12811992 dated Feb. 2, 2015.

* cited by examiner

FIG. 7

SOLID-PHASE EXTRACTION APPARATUS AND VISCOSITY MEASUREMENT APPARATUS

TECHNICAL FIELD

The present invention relates to a solid-phase extraction apparatus that purifies or condenses a measurement component(s) in a sample solution by using a solid-phase extraction cartridge provided with a solid-phase extraction material therein, and the present invention particularly relates to pressure control based on the viscosity of the sample solution in pressurizing extraction in which solid-phase extraction is carried out by introducing pressurized air into the solid-phase extraction cartridge.

BACKGROUND ART

Solid-phase extraction is a method to separate a measurement component(s) and an impurity(ies) in a sample solution from each other based on physical and chemical properties by using a solid substance (solid-phase extraction material) generally referred to as a solid phase. The solid-phase extraction is used for removing the impurities, which disturb analysis in various analysis techniques (liquid chromatograph, mass analysis), to purify the measurement component.

Examples of the sample used in the analysis include urine, blood, water, and soil. If the affinity between a measurement component and the surface of the solid-phase extraction material is high when the sample solution passes through the solid-phase extraction material, the measurement component of the sample solution is selectively adsorbed. Therefore, purification or condensing of the measurement component can be carried out.

As the solid-phase extraction material, generally, particles of organic polymers such as silica gel and styrene-divinylbenzene copolymer or the particles thereof of which surfaces are chemically modified are used.

Steps of the solid-phase extraction are composed of three steps: an adsorbing step in which the measurement component in the sample solution is adsorbed by the solid-phase extraction material, a cleaning step in which the impurities other than the measurement component adsorbed on the solid-phase extraction material are cleaned, and an eluting step in which the measurement component adsorbed on the solid-phase extraction material is eluted.

In the adsorbing step, the measurement component is adsorbed, and the components (impurities) which disturb analysis flow out without being adsorbed. This is a first purification step. However, since some impurities are adsorbed on the solid-phase extraction material, the adsorbed impurities are removed in the cleaning step. This is a second purification step.

In the eluting step, the purified measurement component is separated from the solid-phase extraction material by an eluting solution. The extracted solution after the separation is sent to an analysis apparatus, and the signal intensity of the measurement component is measured. As described above, in the solid-phase extraction, the impurities are removed in the order of the adsorbing, cleaning, and eluting steps, thereby purifying the measurement component.

Examples of the solid-phase extraction apparatus that automatically carries out above-described three steps include: a solid-phase extraction apparatus described in Japanese Patent Application Laid-Open Publication No. H08-164302 (Patent Document 1) that applies a pressure to a sample solution by using a pressurizing mechanism to cause the solution to pass through a solid-phase extraction material and a solid-phase extraction apparatus described in Japanese Patent Application Laid-Open Publication No. 2006-7081 (Patent Document 2) that causes a sample solution to pass through a solid-phase extraction material by using a depressurizing mechanism.

Examples of a different pressurizing-type extraction apparatus include an extraction apparatus described in Japanese Patent Application Laid-Open Publication No. 2005-110670 (Patent Document 3) that determines pressurization condition in accordance with the information corresponding to the type of a sample solution in advance.

CITATION LIST

Patent Documents

Patent Document 1: Japanese Patent Application Laid-Open Publication No. H08-164302
Patent Document 2: Japanese Patent Application Laid-Open Publication No. 2006-7081
Patent Document 3: Japanese Patent Application Laid-Open Publication No. 2005-110670

DISCLOSURE OF THE INVENTION

Problems to be Solved by the Invention

The rate at which the measurement component of the sample solution is adsorbed on the solid-phase extraction material largely depends on the speed at which the sample solution permeates through the solid-phase extraction material. The viscosity, etc. of the sample solution which is generally used in solid-phase extraction are not constant; therefore, the liquid-permeation speed in the adsorbing step is fluctuated, variations are generated in the adsorbing rate, and the accuracy of the collection rate of the measurement component in the eluting step is also decreased. The collection rate herein is the ratio of the amount of the measurement component after the eluting step and the amount of the measurement component in the sample solution.

In this manner, the final analysis accuracy is also decreased. Furthermore, since the liquid-permeation speed is fluctuated, a certain processing ability as an apparatus cannot be ensured.

In the solid-phase extraction of the apparatus described in Patent Document 1, the pressurizing extraction of the sample solution is carried out by the pressure that is set by an operator in advance. In order to obtain a stable collection rate and processing ability of the measurement components with the solid-phase extraction apparatus, the viscosity of the sample solution has to be measured by using another measuring instrument such as a viscometer in advance, leading to increase of the working quantity of the operator, manpower cost, etc.

Moreover, in the solid-phase extraction of the apparatus described in Patent Document 2, a depressurizing method is used. In this apparatus, sample solutions, reagents, etc. are dispensed into a plural-well cartridge provided with the solid-phase extraction material, and suction extraction is carried out. In this method, the sample solutions of the plurality of wells are subjected to suction extraction at the same time; therefore, the liquid-permeation speeds at the respective wells are varied.

Thus, it is extremely difficult to control the liquid-permeation speeds in accordance with the viscosity, etc. of the individual sample solutions. Also in this apparatus, variations are generated in the rate at which the measurement component is adsorbed onto the solid-phase extraction material, and the accuracy of the collection rate of the measurement component is decreased. Furthermore, a certain processing ability cannot be ensured.

In addition, the extraction method described in Patent Document 3 is a method in which the applied pressure is changed in accordance with the type and characteristics of the sample solution. Specifically, with respect to the sample solution for which long time was taken in liquid transfer in the adsorbing step, the pressures applied in the next cleaning step and eluting step are increased, thereby shortening extraction time.

In this method, the extraction time is shortened; however, an extraction process that optimizes the collection rate of the measurement component is not carried out in all of the extraction steps. The viscosity is different since many impurities, etc. are present in the sample solution in the adsorbing step, and variations in the time are the largest among the adsorbing, cleaning, and eluting steps. The solutions used in the cleaning and eluting steps are, for example, reagents, and the viscosities thereof are almost constant; therefore, increase of the applied pressure leads to decrease in the collection rate of the measurement component.

Furthermore, in Patent Document 3, the pressures in the cleaning and eluting steps are controlled by using the liquid feeding time of the adsorbing step; therefore, it is impossible to control the liquid-permeation speed to optimize the collection rate of the measurement component in the adsorbing step. Therefore, also in this apparatus, if the viscosity, etc. of the sample solution are different, variations are generated in the rate of adsorption of the measurement component, and accuracy of the collection rate of the measurement component is decreased.

Thus, currently, there has not been an extraction apparatus that optimally controls the liquid-permeation speed in all the steps of solid-phase extraction, i.e., the adsorbing step, the cleaning step, and the eluting step so as to stabilize the accuracy of the collection rate of the measurement component.

Therefore, it is a preferred aim of the present invention to provide a solid-phase extraction apparatus that is capable of carrying out highly accurate solid-phase extraction by automatically controlling the liquid-permeation speed in the adsorbing step, the cleaning step, and the eluting step of solid-phase extraction in order to improve the accuracy of the collection rate of the measurement component and ensure a certain processing ability also in the measurement of each of sample solutions respectively having different viscosities.

The above and other preferred aims and novel characteristics of the present invention will be apparent from the description of the present specification and the accompanying drawings.

Means for Solving the Problems

The typical ones of the inventions disclosed in the present application will be briefly described as follows.

More specifically, the outline of the typical aspect is a solid-phase extraction apparatus having: a sample dispensing unit that dispenses a sample solution; a solid-phase extraction unit that carries out a solid-phase extraction process of applying a pressure to the sample solution dispensed by the sample dispensing unit and extracting a measurement component from the sample solution; and a converting unit that measures viscosity of the sample solution and determines the pressure based on information of the measured viscosity of the sample solution.

The solid-phase extraction apparatus includes: a pressurizing syringe pump; an air feed pipe; an air-feed-pipe pressure sensor; an electromagnetic valve; a solid-phase extraction cartridge; a sample dispensing nozzle; a sample-dispensing syringe pump; a solution feed pipe; a solution-feed-pipe pressure sensor; and a control unit, and the control unit calculates viscosity of the sample solution based on the pressure measured by the solution-feed-pipe pressure sensor, determines the pressure to be applied to the solid-phase extraction cartridge based on information of the calculated viscosity of the sample solution, and highly accurately controls a collection rate of the measurement component from the sample solution without decreasing the collection rate.

Moreover, a viscosity measurement apparatus includes: a sample dispensing nozzle that suctions and discharges a sample solution; a sample-dispensing syringe pump that carries out operations of suction and discharge of the sample solution; a solution feed pipe that connects the sample dispensing nozzle and the sample-dispensing syringe pump; a solution-feed-pipe pressure sensor that measures a pressure in the solution feed pipe; and a converting unit that calculates viscosity information of the sample solution based on the pressure measured by the solution-feed-pipe pressure sensor.

Effects of the Invention

026 The effect obtained by typical aspects of the present invention will be briefly described below.

More specifically, the effects obtained by the typical aspects is capability of accurately measuring viscosity of a sample solution by monitoring pressure inside a solution feed pipe upon suction of the sample solution so that an accurate liquid-permeation speed can be controlled by adjusting pressure applied in each step of suction, cleaning, and elusion in accordance with the measured viscosity. As a result, the liquid-permeation speed can be kept constant without being affected by the viscosity of the sample solution and thus a certain processing ability can be ensured. Moreover, a stable collection rate of measured components can be obtained and thus accuracy of analysis is improved.

BEST MODE FOR CARRYING OUT THE INVENTION

029 Hereinafter, embodiments of the present invention will be described in detail with reference to the accompanying drawings. Note that components having the same function are denoted by the same reference symbols throughout the drawings for describing the embodiment, and the repetitive description thereof will be omitted.

<Schematic Configuration of Solid-Phase Extraction Apparatus>

Figure 1:
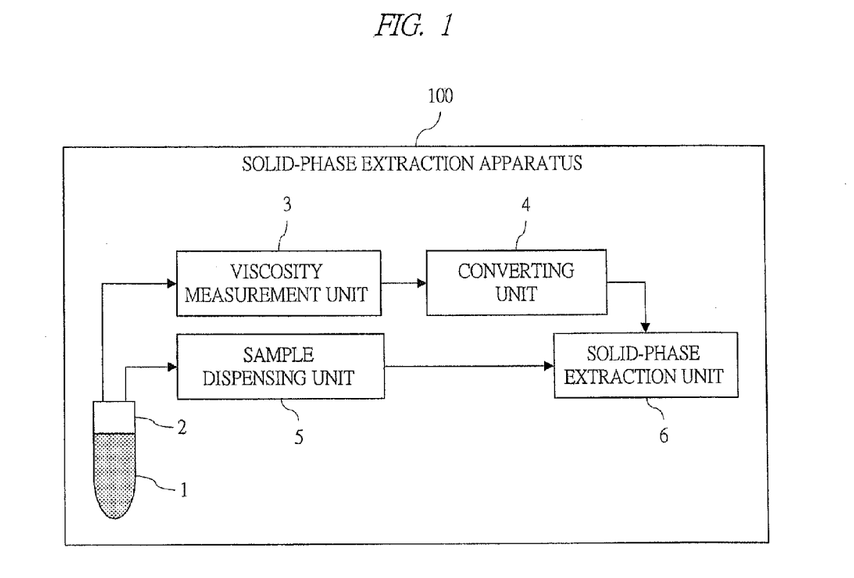
FIG. 1 is a block diagram showing a schematic configuration of a solid-phase extraction apparatus according to a first embodiment of the present invention.

With reference to FIG. 1, a schematic configuration of a solid-phase extraction apparatus according to a first embodiment of the present invention will be described. FIG. 1 is a block diagram showing the schematic configuration of the solid-phase extraction apparatus according to the first embodiment of the present invention.

In FIG. 1, the solid-phase extraction apparatus 100 is composed of a viscosity measurement unit 3, a converting unit 4, a sample dispensing unit 5, and a solid-phase extraction unit 6; and a sample container(s) 2 containing a sample solution(s) 1 is installed to carry out solid-phase extraction.

In the solid-phase extraction apparatus 100, the sample container 2 containing the sample solution 1 is installed in the solid-phase extraction apparatus 100, and the viscosity of the sample solution 1 is measured by the viscosity measurement unit 3. Next, in the converting unit 4, the pressure used in solid-phase extraction is calculated based on the information measured by the viscosity measurement unit 3.

The sample solution 1 is sent to the solid-phase extraction unit 6 via the sample dispensing unit 5. In the solid-phase extraction unit 6, solid-phase extraction is carried out by application of the pressure calculated by the converting unit 4 and pressure reduction.

<Overall Configuration of Solid-Phase Extraction Apparatus>

Figure 2:
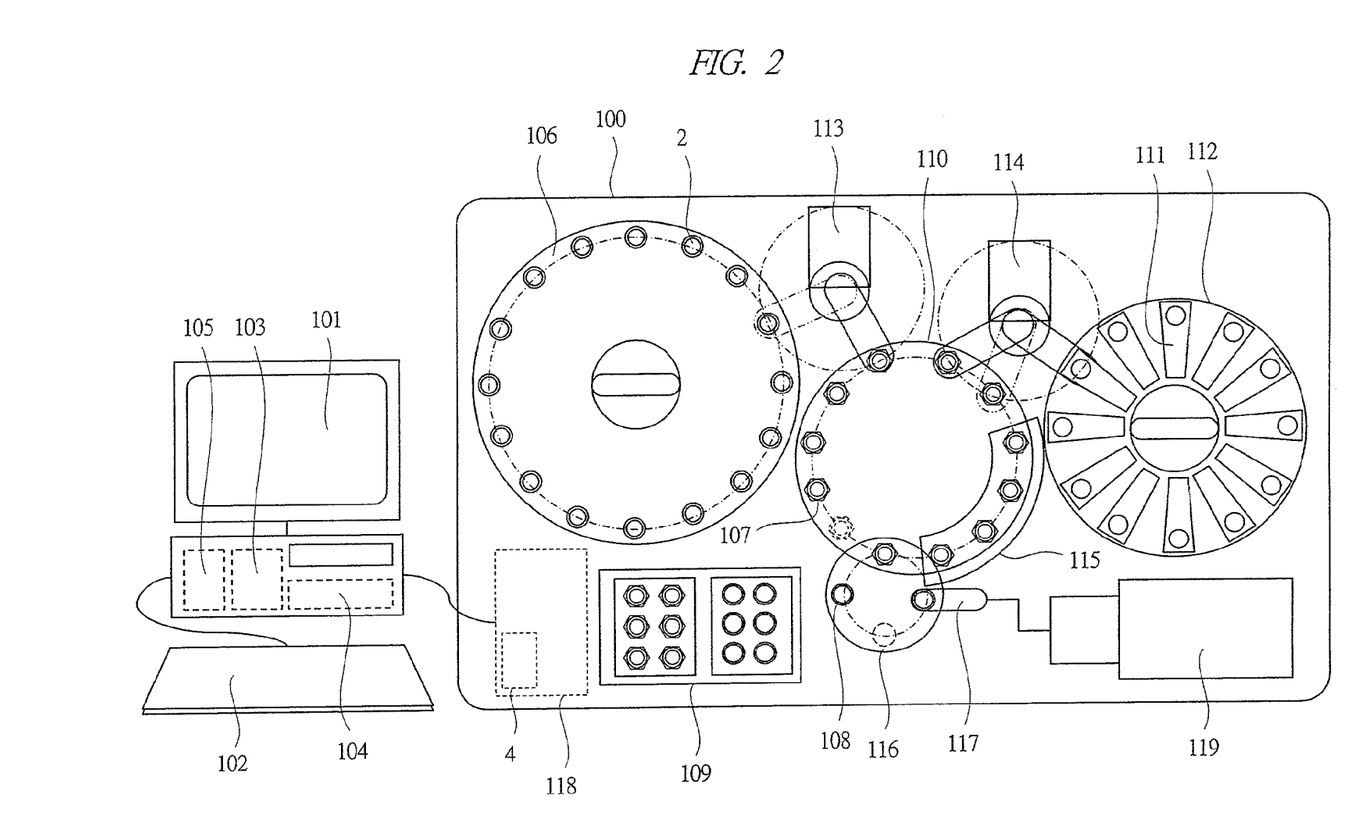
FIG. 2 is a configuration diagram showing an overall configuration of a solid-phase extraction apparatus according to the first embodiment of the present invention.

Next, with reference to FIG. 2, an overall configuration of the solid-phase extraction apparatus according to the first embodiment of the present invention will be described. FIG. 2 is a configuration diagram showing the overall configuration of the solid-phase extraction apparatus according to the first embodiment of the present invention and is showing a plan view.

In FIG. 2, the solid-phase extraction apparatus 100 is composed of: an operation-panel-equipped panel display unit 101; an input unit 102; a calculation processing unit 103; a storage unit 104; an external communication interface unit 105, which carries out communication processing with outside; the sample containers 2 into which sample solutions to be subjected to extraction processes have been dispensed; a sample installation unit 106 in which the sample containers 2 are disposed; solid-phase extraction cartridges 107; extraction containers 108; an installation unit 109, which stores the solid-phase extraction cartridges 107 and the extraction containers 108 before usage; a processing unit 110, which carries out solid-phase extraction processes by using the solid-phase extraction cartridges 107; reagent containers 111, which store cleaning solutions and eluting solutions used in the solid-phase extraction processes; a reagent disposition unit 112, in which the reagent containers 111 are disposed; a sample dispensing mechanism 113 (the sample dispensing unit 5), which dispenses samples into the solid-phase extraction cartridges; a reagent dispensing mechanism 114, which dispenses reagents into the solid-phase extraction cartridges; a solid-phase-extraction processing unit 115 (the solid-phase extraction unit 6), which carries out extraction processes; an extraction-container installation unit 116, in which the extraction containers are disposed; an extracted-sample-solution dispensing mechanism 117, which dispenses extracted sample solutions; and a control unit 118, which controls mechanism elements.

Furthermore, a detection unit 119, which measures a measurement component(s) by using extraction treatment samples, which have undergone solid-phase extraction, is coupled. Herein, the detection unit 119 is a detector which can be used for measuring targets or may be a photometer, a mass spectrometer, or another detector.

<Operation of Solid-Phase Extraction>

Figure 3:
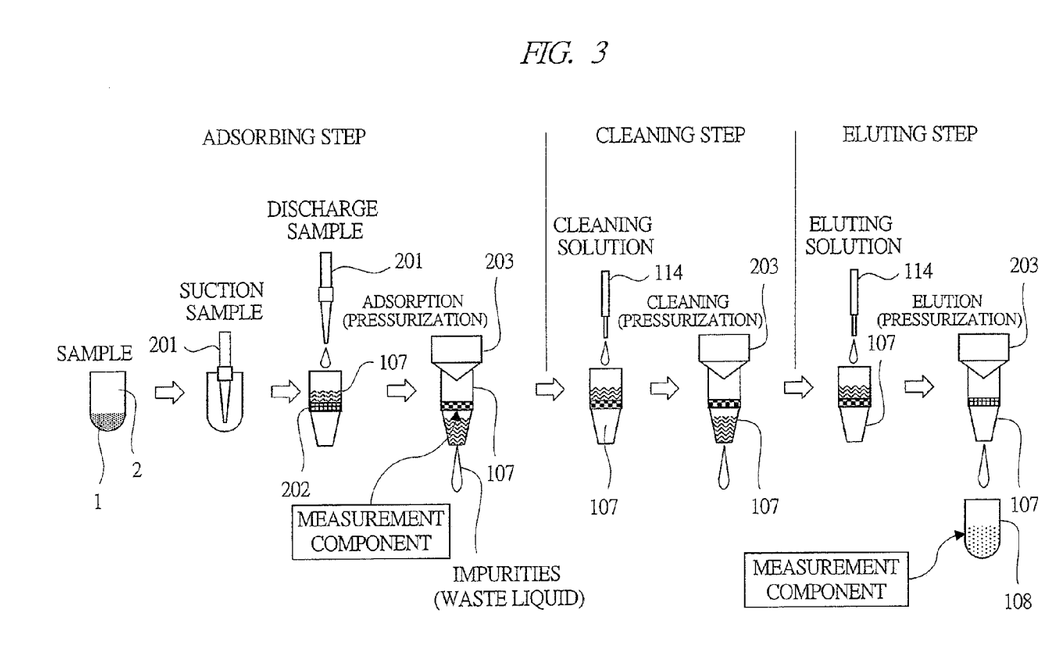
FIG. 3 is an explanatory diagram for explaining operations of solid-phase extraction of the solid-phase extraction apparatus according to the first embodiment of the present invention.

Next, according to FIG. 2 and FIG. 3, an operation of solid-phase extraction of the solid-phase extraction apparatus according to the first embodiment of the present invention will be explained. FIG. 3 is an explanatory diagram for explaining the operation of solid-phase extraction of the solid-phase extraction apparatus according to the first embodiment of the present invention.

First, a solid-phase extraction material 202 is sealed in the solid-phase extraction cartridge 107 used in the solid-phase extraction apparatus 100.

The solid-phase extraction apparatus 100 sequentially moves the cartridges by moving the processing unit 110 on which the solid-phase extraction cartridges 107 are installed, suctions the sample solutions 1 in the dispensing amounts according to extraction conditions stored in the apparatus from the sample containers 2 by a sample dispensing nozzle 201 of the sample dispensing mechanism 113 based on information of the sample solutions 1, etc. input by an operator with the input unit 102 or the panel display unit 101 of the solid-phase extraction apparatus 100, and dispenses the solutions to the solid-phase extraction cartridges 107.

The solid-phase extraction cartridges 107 to which the sample solutions 1 have been dispensed are moved to the solid-phase-extraction processing unit 115.

In the present embodiment, since the processing unit 110 has a circular table shape, the movement is carried out by rotary motion. In the solid-phase-extraction processing unit 115, after the solid-phase extraction cartridge 107 and an extraction nozzle 203 are joined with each other, air is supplied.

As a result of air supply, the sample solution 1 passes through the solid-phase extraction material 202, and a measurement component(s) is absorbed on the solid-phase extraction material 202. In this process, impurities are discharged. Next, the solid-phase extraction cartridge 107 is subjected to cleaning treatment in a state in which the measurement component is adsorbed on the solid-phase extraction material 202.

In a cleaning step, the cleaning reagent in the reagent container 111 is suctioned by the reagent dispensing mechanism 114 and discharged to the solid-phase extraction cartridge 107. The discharged cleaning reagent is caused to pass through the solid-phase extraction material 202 by supply of air from the extraction nozzle 203 of the solid-phase-extraction processing unit 115.

Upon passing, the impurities in the sample solution 1 present on the surface of the solid-phase extraction material 202 are discharged together with the cleaning solution.

In an eluting step, the eluting solution is suctioned by the reagent dispensing mechanism 114 from the reagent container 111 and discharged to the solid-phase extraction cartridge 107. The discharged eluting solution passes through the solid-phase extraction material 202 by supply of air from the extraction nozzle 203 of the solid-phase extraction processing unit 115 and elutes a measurement component(s).

In this process, the liquid which has become an extracted sample solution is received by the extraction container 108 therebelow. The extraction container 108 is moved to the position of the extracted-sample-solution dispensing mechanism 117 by moving the extraction-container installation unit 116, the extracted sample solution in the extraction container 108 is sent to the detection unit 119 at this point, and detection of the measurement component is carried out.

Outputs of the detection unit 119 undergo concentration calculations, unit converting processes, etc. by the calculation processing unit 103, are displayed by the panel display unit 101 as desired measurement results, and are saved in the storage unit 104 together with the information of the sample.

By such a series of operations of solid-phase extraction, the extracted sample solution containing the measurement component can be obtained. Generally, the content of the measurement component is measured by measuring the extracted sample solution, from which the impurities in the sample have been discharged by the solid-phase extraction, by measurement equipment such as a photometer and a mass spectrometer.

The pressurization caused by supply of air of the extraction nozzle 203 in the above-described process is controlled by the converting unit 4 and the control unit 118 based on the viscosity of the sample obtained by the viscosity measurement unit 3 shown in FIG. 1. Hereinafter, pressurization control will be explained.

<Relation Between Liquid-Permeation Speed and Collection Rate of Measurement Component in Pressurization Controlling Process>

Figure 4A:
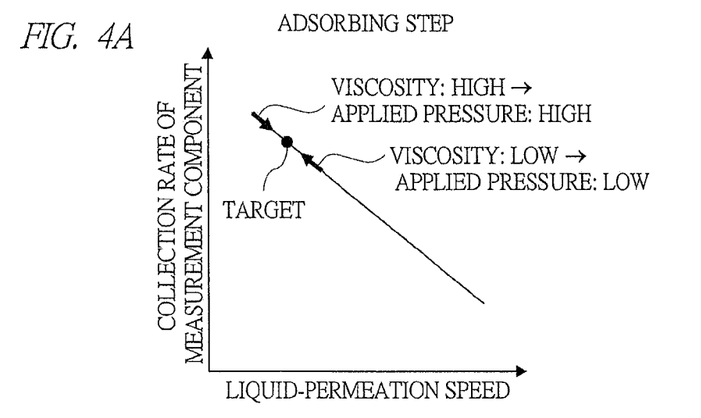
FIGS. 4A to 4C are drawings showing relations between liquid-permeation speeds and collection rates of measurement components in pressurization control in a solid-phase extraction process of the solid-phase extraction apparatus according to the first embodiment of the present invention.
Figure 4B:
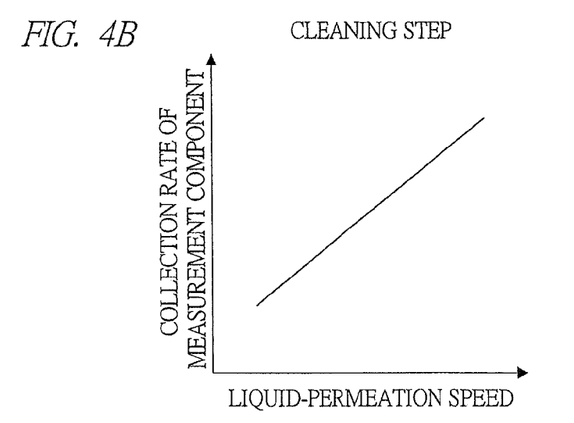
Figure 4C:
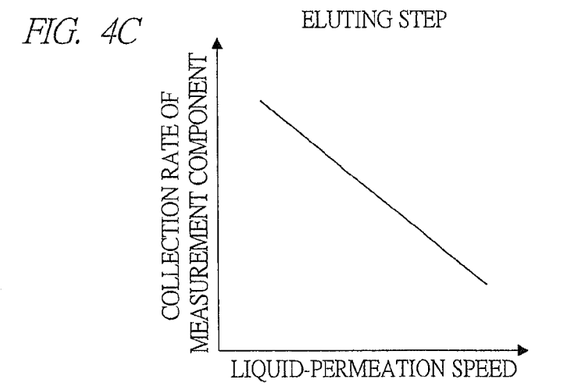

Next, according to FIG. 4, the relation between a liquid-permeation speed and the collection rate of the measurement component in the pressurization control in the solid-phase extraction process of the solid-phase extraction apparatus 100 according to the first embodiment of the present invention will be explained. FIGS. 4A, 4B and 4C are drawings showing the relations between the liquid-permeation speed and the collection rate of the measurement component in the pressurization control in the solid-phase extraction process of the solid-phase extraction apparatus 100 according to the first embodiment of the present invention. FIG. 4A shows the adsorbing step, FIG. 4B shows the cleaning step, and FIG. 4C shows the eluting step, wherein horizontal axes show the liquid-permeation speed proportional to the pressure of pressurization, and vertical axes show the collection rate of the measurement component.

As shown in FIG. 4A, in the adsorbing step, if the liquid-permeation speed is too high, the measurement component cannot be adsorbed. Therefore, when the liquid-permeation speed is increased, the collection rate is monotonically decreased.

As shown in FIG. 4B, in the cleaning step, if the liquid-permeation speed is too low, the adsorbed measurement component is eventually eluted and washed out. More specifically, if the liquid-permeation speed is increased, the collection rate is monotonically increased.

As shown in FIG. 4C, in the eluting step, if the liquid-permeation speed is too high, the time for elution becomes insufficient, and the collection rate is therefore decreased. More specifically, if the liquid-permeation speed is increased, the collection rate is monotonically decreased.

The collection rate of all the steps is the multiplication of FIG. 4A, FIG. 4B, and FIG. 4C, and there are liquid-permeation speeds for obtaining an optimum collection rate for each measurement component. Also, since the relation between the liquid-permeation speed and the collection rate of the measurement content in each step depends on the affinity level between the measurement component, the solid-phase extraction agent, and a solvent, the liquid-permeation speed has to be controlled for each measurement component.

Therefore, in order to obtain an optimum collection rate, the liquid-permeation speeds of the three steps are independently controlled and optimized. As is known by Poiseuille's formula, the liquid-permeation speed is inversely proportional to viscosity and is proportional to the pressure.

In the present embodiment, in order to control the liquid-permeation speeds, the viscosity of the sample solution 1 is measured, and the pressure to be applied to the sample solution 1 in the solid-phase extraction is calculated and controlled by (the converting unit 4 in) the control unit 118 based on the measured value. Specifically, as shown in FIG. 4A, the pressure to be applied is increased if the viscosity is high, and the pressure to be applied is decreased if the viscosity is low, thereby getting close to a target liquid-permeation speed.

The collection rate of the measurement component can be optimized by measuring the viscosity of the sample solution 1 and controlling the pressure in this manner.

FIGS. 4A, 4B, and 4C show an example in which, in the adsorbing step and the eluting step, the collection rate of the measurement component is decreased if the liquid-permeation speed is increased, and, in the cleaning step, the collection rate of the measurement component is increased if the liquid-permeation speed is increased. However, these relations are not limited thereto depending on the type of the sample, and some samples show collection rate changes which are different therefrom. Even in such a case, the collection rate can be optimized by independently controlling and optimizing the liquid-permeation speeds of the three steps in order to obtain an optimum collection rate.

<Viscosity Measurement Method>

Figure 5A:
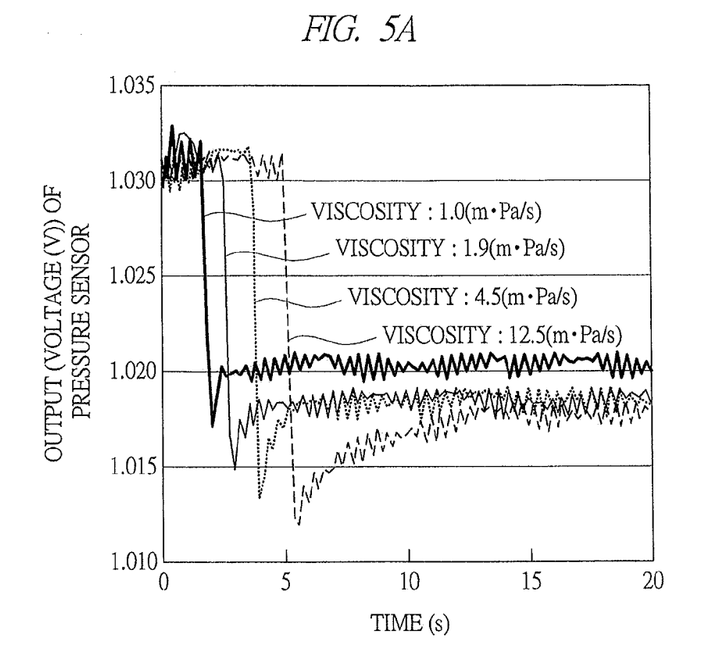
FIGS. 5A and 5B are explanatory diagrams for explaining a measurement method of viscosity by a viscosity measurement unit of the solid-phase extraction apparatus according to the first embodiment of the present invention.
Figure 5B:
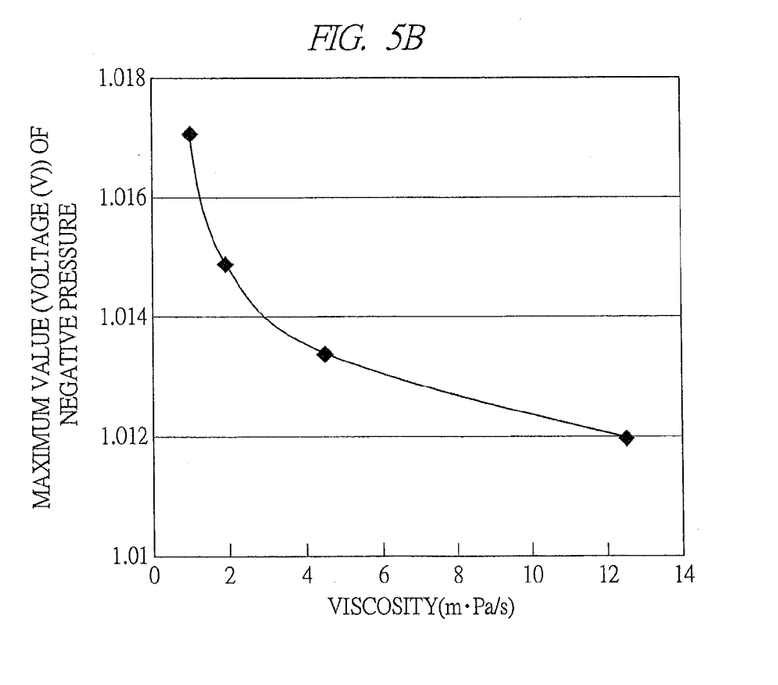

Next, according to FIG. 5, a viscosity measurement method by the viscosity measurement unit of the solid-phase extraction apparatus 100 according to the first embodiment of the present invention will be explained. FIGS. 5A and 5B are explanatory diagrams for explaining the viscosity measurement method by the viscosity measurement unit of the solid-phase extraction apparatus 100 according to the first embodiment of the present invention. In FIG. 5A, the horizontal axis shows measurement time, and the vertical axis shows outputs of a pressure sensor showing the pressures in the sample dispensing nozzle 201. In FIG. 5B, the horizontal axis shows viscosity, and the vertical axis shows the maximum values of negative pressures detected along with elapse of the measurement time of FIG. 5A.

In the present embodiment, the viscosity of the sample solution 1 is calculated by the pressure in the sample dispensing nozzle 201.

Specifically, as shown in FIG. 5A, when the sample solution 1 is suctioned by the sample dispensing nozzle 201, the pressure in the sample dispensing nozzle 201 becomes a negative pressure, and the maximum value of the negative pressure and the time taken until a steady state is obtained are different depending on the viscosity.

The converting unit 4 in the control unit 118 calculates the viscosity of the sample solution 1 from, for example, the maximum value of the measured negative pressures, the difference between the atmospheric pressure and the maximum value of the measured negative pressure, the time taken until a steady state is obtained, or an integral value of a pressure obtained until a steady state is obtained.

The maximum value of the negative pressure in the sample dispensing nozzle 201, for example, has a relation as shown in FIG. 5B, and the viscosity is calculated in accordance with the maximum value of the negative pressure in the sample dispensing nozzle 201 by a function stored in the control unit 118.

The converting unit 4 in the control unit 118 determines the pressure, which is to be applied in accordance with the viscosity calculated by the converting unit 4 in the control unit 118, so as to optimize the collection rate of the measurement component and controls the liquid-permeation speed.

In the example shown in FIG. 5B, an example of the maximum values of the negative pressures is shown. However, other than that, the difference between the atmospheric pressure and the maximum value of the measured negative pressures, the time taken until a steady state is obtained, the integral value of the pressure obtained until a steady state is obtained, and so on are related to the viscosity; and the viscosity can be calculated by storing them as functions in the control unit 118 or the converting unit 4.

As a measuring instrument which measures the viscosity of the sample solution 1, a viscometer or another measuring instrument may be used.

<Specific Configuration of Viscosity Measurement Unit and Pressurized-Air Supplying Unit>

Figure 6:
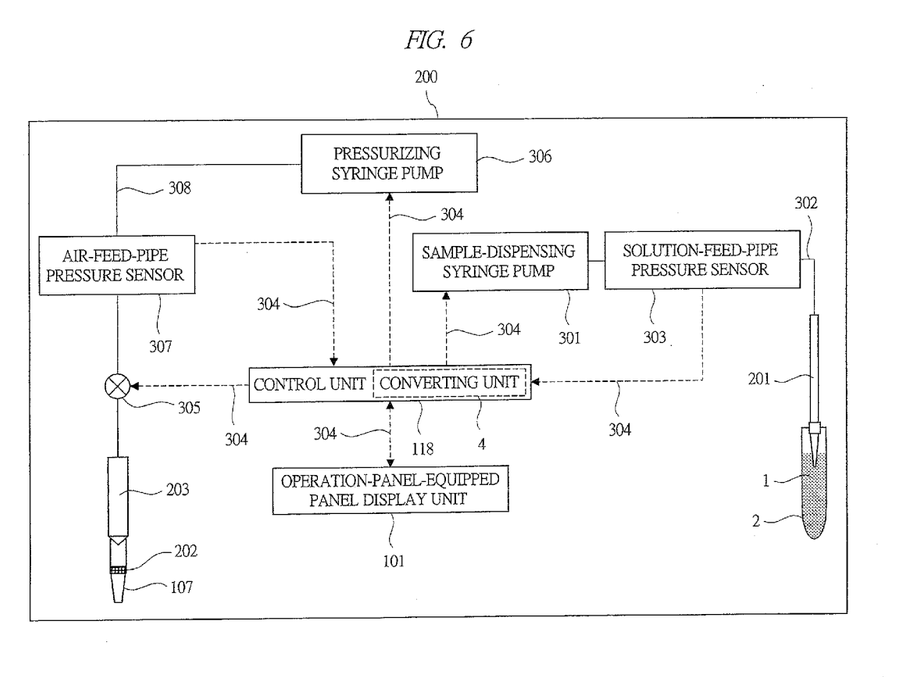
FIG. 6 is an explanatory diagram for explaining specific configurations of the viscosity measurement unit and a pressurized-air supplying unit of the solid-phase extraction apparatus according to the first embodiment of the present invention.

Next, according to FIG. 6, specific configurations of the viscosity measurement unit and a pressurized-air supplying unit of the solid-phase extraction apparatus 100 according to the first embodiment of the present invention will be explained. FIG. 6 is an explanatory diagram for explaining the specific configurations of the viscosity measurement unit and the pressurized-air supplying unit of the solid-phase extraction apparatus 100 according to the first embodiment of the present invention and is showing a control system diagram of a pressurized-air supplying mechanism.

In FIG. 6, the pressurized-air supplying mechanism 200 is composed of: the sample dispensing nozzle 201; a sample-dispensing syringe pump 301 for suctioning the sample solution 1; a solution feed pipe 302, which connects the sample-dispensing syringe pump 301 and the sample dispensing nozzle 201; a solution-feed-pipe pressure sensor 303, which measures the pressure in the sample-dispensing nozzle 201; a pressurizing syringe pump 306 for applying pressures; the extraction nozzle 203 for feeding air to the solid-phase extraction cartridge 107; an air feed pipe 308, which connects the pressurizing syringe pump 306 and the extraction nozzle 203; an air-feed-pipe pressure sensor 307, which measures the pressure in the air feed pipe 308; an electromagnetic valve 305 for maintaining the pressure in the air feed pipe 308 to a high pressure; the control unit 118, the converting unit 4, and the operation-panel-equipped display unit 101. Electric signals are represented by 304.

Moreover, the sample dispensing nozzle 201, the sample-dispensing syringe pump 301, the solution feed pipe 302, the solution-feed-pipe pressure sensor 303, the control unit 118, the converting unit 4, and the operation-panel-equipped panel display unit 101 constitute a viscosity measurement apparatus.

The viscosity measurement unit 3 in FIG. 1 corresponds to pressure measurement by the solution-feed-pipe pressure sensor 303 and processing of the calculation of viscosity by the converting unit 4 in the control unit 118 based on the measured value thereof.

In the present invention, the converting unit 4 is installed in the control unit 118. However, the converting unit 4 may be in the solution-feed-pipe pressure sensor 303 or at another location. Furthermore, a plurality of converting units 4 may be present.

<Pressurization Controlling Process>

Figure 7:
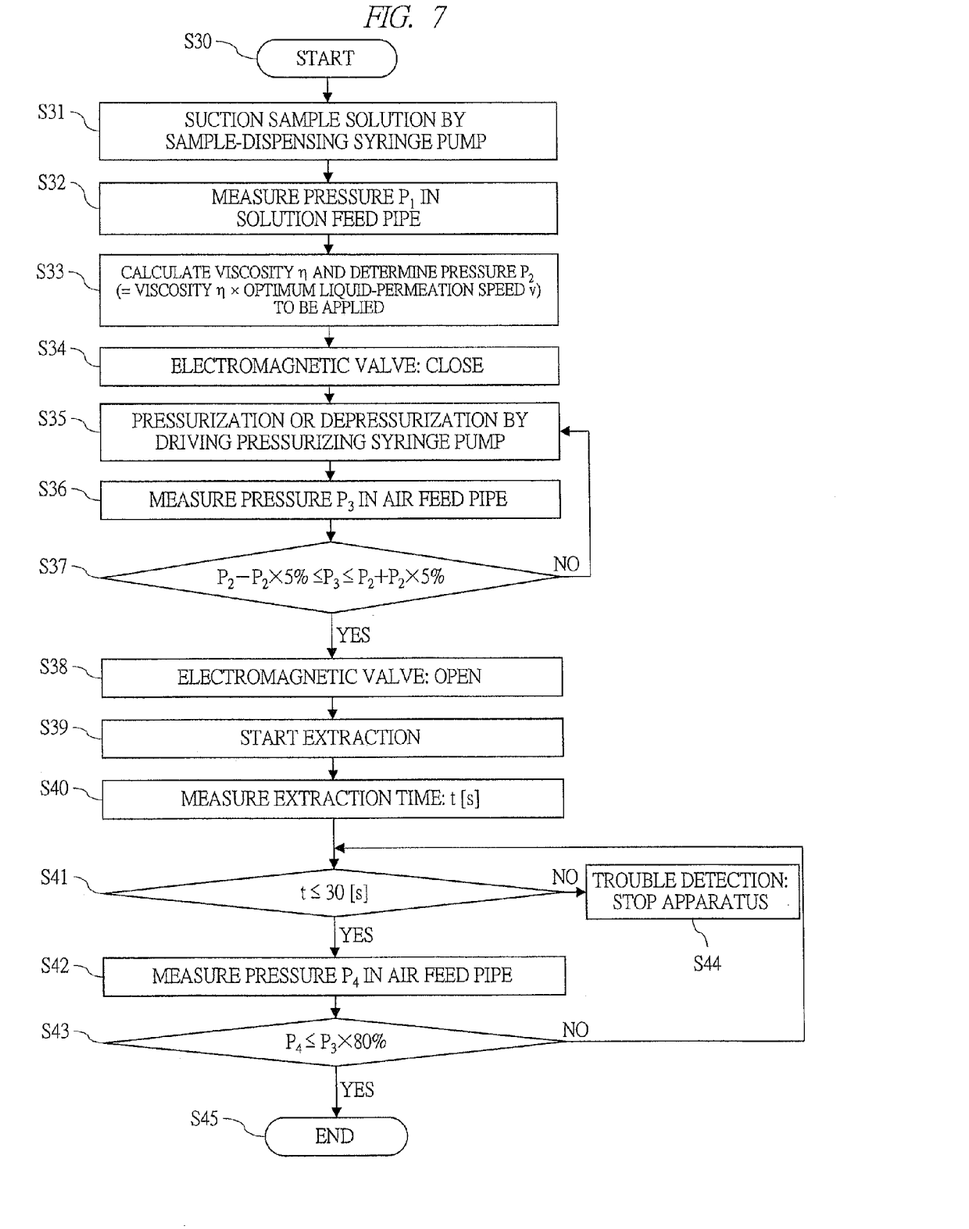
FIG. 7 is a flow chart showing a pressurization controlling process of the solid-phase extraction apparatus according to the first embodiment of the present invention.

Next, according to FIG. 6 and FIG. 7, a pressurization controlling process of the solid-phase extraction apparatus 100 according to the first embodiment of the present invention will be explained. FIG. 7 is a flow chart showing the pressurization controlling process of the solid-phase extraction apparatus 100 according to the first embodiment of the present invention.

First, the electric signal 304 of an input value from the operation-panel-equipped panel display unit 101 or the input unit 102 is received by the control unit 118, pressurization control is started (S30).

The electric signal 304 of the input value from the panel display unit 101 or the input unit 102 is converted to a drive volume of the sample-dispensing syringe pump 301 by the control unit 118 and is transmitted to the sample-dispensing syringe pump 301 as the electric signal 304. The sample-dispensing syringe pump 301 is driven in accordance with the drive volume of the electric signal 304 and suctions the sample solution 1 from the sample dispensing nozzle 201 (S31).

During a suction operation of the sample solution 1, the pressure $P_1$ in the solution feed pipe 302 is measured by the solution-feed-pipe pressure sensor 303, and the electric signal 304 of the pressure $P_1$ is transmitted to the converting unit 4 in the control unit 118 (S32).

The sample dispensing nozzle 201 discharges the suctioned sample solution 1 into the solid-phase extraction cartridge 107. The converting unit 4 in the control unit 118 calculates viscosity $\eta$ based on the value of the pressure $P_1$ received from the solution-feed-pipe pressure sensor 303 and determines the pressure $P_2$ to be applied to the sample solution 1, which has been dispensed into the solid-phase extraction cartridge 107, and the drive volume of the pressurizing syringe pump 306 (S33).

The pressure $P_2$ is the product of the liquid-permeation speed v, which is stored in the converting unit 4 in the control unit 118 and at which the collection rate of each measurement component is optimized, and the viscosity $\mu$ of the sample solution 1.

Next, the control unit 118 transmits the electric signal 304 to the electromagnetic valve 305 and closes the electromagnetic valve 305 (S34). Then, the control unit 118 transmits the electric signal 304 of the drive volume of the pressurizing syringe pump 306 to the pressurizing syringe pump 306 to drive the pressurizing syringe pump 306 and increase the pressure in the air feed pipe 308 to a high pressure (S35).

In this process, the pressure $P_3$ in the air feed pipe 308 is measured by the air-feed-pipe pressure sensor 307, and the electric signal 304 of the pressure $P_3$ is transmitted to the control unit 118 (S36). The control unit 118 determines whether the difference between the pressure $P_3$ and the applied pressure $P_2$ is within ±5% of $P_2$ or not ($P_2-P_2\times 5\% \leq P_3 \leq P_2+P_2\times 5\%$) (S37).

If the condition is not satisfied in S37, the drive volume of the pressurizing syringe pump 306 is determined again, and the electric signal 304 of the drive volume is transmitted from the control unit 118 to the pressurizing syringe pump 306 to increase or decrease the pressure in the air feed pipe 308 (S35).

The operations of S35, S36, and S37 are repeated until the condition is satisfied. If the condition is satisfied in S37, after the extraction nozzle 203 and the solid-phase extraction cartridge 107 are coupled to each other, the electric signal 304 is transmitted from the control unit 118 to the electromagnetic valve 305 to open the electromagnetic valve 305 (S38).

When the electromagnetic valve 305 is opened, the pressure $P_3$ in the air feed pipe 308 is released, and extraction is started (S39). Immediately after the extraction is started, measurement of extraction time t (s) is started in the control unit 118 (S40).

Next, whether the extraction time t is equal to or less than 30 (s) or not is determined (t≤30) (S41). If the condition is not satisfied in S41, trouble detection is determined, and the apparatus is stopped (S44). In that process, the electric signal 304 is transmitted from the control unit 118 to the panel display unit 101 to display an emergency stop screen on the operation-panel-equipped panel display unit 101.

If the condition is satisfied in S41, the pressure $P_4$ in the air feed pipe 308 is detected by the air-feed-pipe pressure sensor 307 (S42).

Next, the electric signal 304 of the pressure $P_4$ is transmitted to the control unit 118, and whether the pressure $P_4$ is equal to or less than 80% of the pressure $P_3$ in the air feed pipe 308 is determined ($P_4 \leq P_3 \times 80\%$) (S43). If the condition is not satisfied in S43, the process returns to S41. If the condition is satisfied in S43, the pressurization control is normally terminated (S45).

In this manner, in the present embodiment, the collection rate of the measurement component can be optimized by calculating the viscosity $\eta$ of the sample solution 1 and determining the pressure to be applied based on the information of the calculated viscosity $\eta$ and the information of the liquid-permeation speed at which the collection rate of the measurement component is optimized.

In the present embodiment, the case in which there is single extraction component has been explained. However, for example, in a case in which a plurality of measurement components are subjected to the solid-phase extraction process from the sample solution 1 at the same time, the pressure is controlled so that the applied pressure is a pressure that minimizes the difference between the collection rates of the plurality of measurement components, or the pressure can be controlled so that the applied pressure is a pressure that maximizes the average value of the collection rates of the plurality of measurement components.

In the foregoing, the invention made by the present inventors has been described in detail based on the embodiment. However, the present invention is not limited to the above-described embodiment, and it goes without saying that various modifications can be made within a range not departing from the gist of the present invention.

The present invention relates to a solid-phase extraction apparatus that purifies or condenses a measurement component(s) in a sample solution by using a solid-phase extraction cartridge provided with a solid-phase extraction material therein and can be widely applied to an apparatus and a system that carry out pressure control in pressurizing extraction, in which solid-phase extraction is carried out by introducing pressurized air into the solid-phase extraction cartridge.

The invention claimed is:

1. A solid-phase extraction apparatus comprising:
   a pressurizing syringe pump that carries out operations of suction and discharge of air;
   an air feed pipe that feeds the air;
   an air-feed-pipe pressure sensor that monitors a pressure in the air feed pipe;
   a solid-phase extraction cartridge provided with a solid-phase extraction material;
   a sample dispensing nozzle that suctions and discharges a sample solution;
   a sample-dispensing syringe pump that carries out operations of suction and discharge of the sample solution;
   a solution feed pipe that connects the sample dispensing nozzle and the sample-dispensing syringe pump;
   a solution-feed-pipe pressure sensor that measures a pressure in the solution feed pipe; and
   a control unit that is configured to carry out a solid-phase extraction process of operating the sample-dispensing syringe pump, suctioning the sample solution from the sample dispensing nozzle, discharging the sample solution to the solid-phase extraction cartridge, operating the pressurizing syringe pump, feeding the air to the sample solution in the solid-phase extraction cartridge to apply pressure to the solid-phase extraction cartridge, and extracting a measurement component from the sample solution,
   wherein the syringe pump applies a pressure to the sample solution to make the measurement component in the sample solution adsorbed on the solid-phase extraction material, applies pressure to a cleaning solution to make impurities other than the measurement component cleaned from the solid-phase extraction material after the adsorption, and applies a pressure to an eluting solution to make the measurement component eluted from the solid-phase extraction material after the cleaning,
   wherein the control unit has a converting unit that configured to determine the pressure to be applied to the sample solution of the solid-phase extraction cartridge in the adsorption based on the pressure measured by the solution-feed-pipe pressure sensor during the suction of the sample solution; and
   wherein, upon extracting a plurality of the measurement components at the same time, the converting unit is further configured to determine, based on information of the viscosity of the sample solution, the pressure to be applied upon the adsorption of the measurement components in the sample solution so that a difference in collection rate of the plurality of measurement components is minimum, or to determine, based on the information of the viscosity of the sample solution, the pressure to be applied upon the adsorption of the measurement components in the sample solution so that an average value of the collection rate of the plurality of measurement components is maximum.

2. The solid-phase extraction apparatus according to claim 1,
   wherein the converting unit is further configured to calculate the information of the viscosity based on at least one of: a maximum value of a negative pressure generated when the sample solution is suctioned by the sample dispensing nozzle, a difference between an atmospheric pressure and the maximum value of the negative pressure, a time taken until a pressure reaches a steady state is obtained after the sample solution is suctioned, or an integral value of a pressure obtained until the steady state is obtained.

3. The solid-phase extraction apparatus according to claim 1,
wherein the control unit is configured to control a liquid-permeation speed during the adsorption of the sample solution to the solid-phase extraction material, the cleaning of the impurities, and the eluting of the measurement component from the solid-phase extraction material, by adjusting the pressure applied during the adsorption, the cleaning, and the eluting in accordance with the information of the viscosity.

4. The solid-phase extraction system according to claim 3, wherein the control unit is configured to adjust the pressure applied during the adsorption, the cleaning, and the eluting in accordance with the information of the viscosity, in order to keep the liquid-permeation speed constant.

5. The solid-phase extraction system according to claim 1, wherein the information of the viscosity is based on the pressure measured by the solution-feed-pipe pressure sensor.

6. The solid-phase extraction system according to claim 1, wherein, upon eluting a plurality of the measurement components at the same time, the converting unit is further configured to determine, based on the information of the viscosity of the sample solution, the pressure to be applied upon the adsorption of the measurement components in the sample solution so that a difference in collection rate of the plurality of measurement components is minimum, or to determine, based on the information of the viscosity of the sample solution, the pressure to be applied upon the adsorption of the measurement components in the sample solution so that an average value of the collection rate of the plurality of measurement components is maximum.

7. The solid-phase extraction apparatus according to claim 1,
wherein the converting unit is further configured to calculate the viscosity based on a maximum value of a negative pressure generated when the sample solution is suctioned by the sample dispensing nozzle.

8. The solid-phase extraction apparatus according to claim 1,
wherein the converting unit is further configured to calculate the viscosity based on a difference between an atmospheric pressure and the maximum value of a negative pressure generated when the sample solution is suctioned by the sample dispensing nozzle.

9. The solid-phase extraction apparatus according to claim 1,
wherein the converting unit is further configured to calculate the viscosity based on a time taken until a pressure reaches a steady state is obtained after the sample solution is suctioned by the sample dispensing nozzle.

10. The solid-phase extraction apparatus according to claim 1,
wherein the converting unit is further configured to calculate the viscosity based on an integral value of a pressure obtained until the pressure reaches a steady state.

* * * * *